(12) United States Patent
Aitken-Christie et al.

(10) Patent No.: US 6,180,405 B1
(45) Date of Patent: Jan. 30, 2001

(54) STARVATION AND STORAGE OF MATURE SOMATIC EMBRYOS

(75) Inventors: Jennifer Aitken-Christie; Keiko Gough, both of Rotorua (NZ)

(73) Assignee: Carter Holt Harvey Limited, Manukau City (NZ)

( * ) Notice: Under 35 U.S.C. 154(b), the term of this patent shall be extended for 0 days.

(21) Appl. No.: 08/952,518

(22) PCT Filed: May 21, 1996

(86) PCT No.: PCT/NZ96/00047

§ 371 Date: Jan. 29, 1998

§ 102(e) Date: Jan. 29, 1998

(87) PCT Pub. No.: WO96/37095

PCT Pub. Date: Nov. 28, 1996

(30) Foreign Application Priority Data

May 25, 1995 (NZ) .................................... 272210

(51) Int. Cl.[7] ..................................... C12N 5/00
(52) U.S. Cl. .................... 435/422; 435/430; 435/430.1; 47/58.1
(58) Field of Search .................... 435/422, 430, 435/430.1; 47/58.1

(56) References Cited

U.S. PATENT DOCUMENTS

| 4,615,141 | 10/1986 | Janick et al. . |
|---|---|---|
| 4,957,866 | 9/1990 | Gupta et al. . |
| 5,036,007 | 7/1991 | Gupta et al. . |
| 5,041,382 | 8/1991 | Gupta et al. . |
| 5,183,757 | 2/1993 | Roberts . |
| 5,236,841 | 8/1993 | Gupta et al. . |
| 5,238,835 | 8/1993 | McKersie et al. . |
| 5,250,082 | 10/1993 | Teng et al. . |

FOREIGN PATENT DOCUMENTS

| 0408922 | 1/1991 | (EP) . |
|---|---|---|
| 237009 | 11/1992 | (NZ) . |
| 232834 | 1/1993 | (NZ) . |
| 676016 | 4/1994 | (NZ) . |
| 272211 | 5/1995 | (NZ) . |
| 272365 | 6/1995 | (NZ) . |
| WO89/05575 | 6/1989 | (WO) . |
| WO91/01629 | 2/1991 | (WO) . |
| WO93/11660 | 6/1993 | (WO) . |
| WO94/24847 | 11/1994 | (WO) . |
| 93/4807 | 7/1993 | (ZA) . |

OTHER PUBLICATIONS

Lelu, M.A., Bastien, C., Klimaszewska, K., "An Improved Method for Somatic Plantlet Production in Hybrid Larch . . . ", *Plant Cell, Tissue and Organ Culture* 36: 117–127, 1994.

Primary Examiner—Leon B. Lankford, Jr.
(74) Attorney, Agent, or Firm—Jacobson, Price, Holman & Stern, PLLC

(57) ABSTRACT

Mature somatic embryos are treated to provide viable storage over time. The embryos are placed on a gas permeable membrane which separates the embryos from a water source preferably a water-containing matrix. The system is sealed in a gas environment while the embryos are starved.

29 Claims, 3 Drawing Sheets

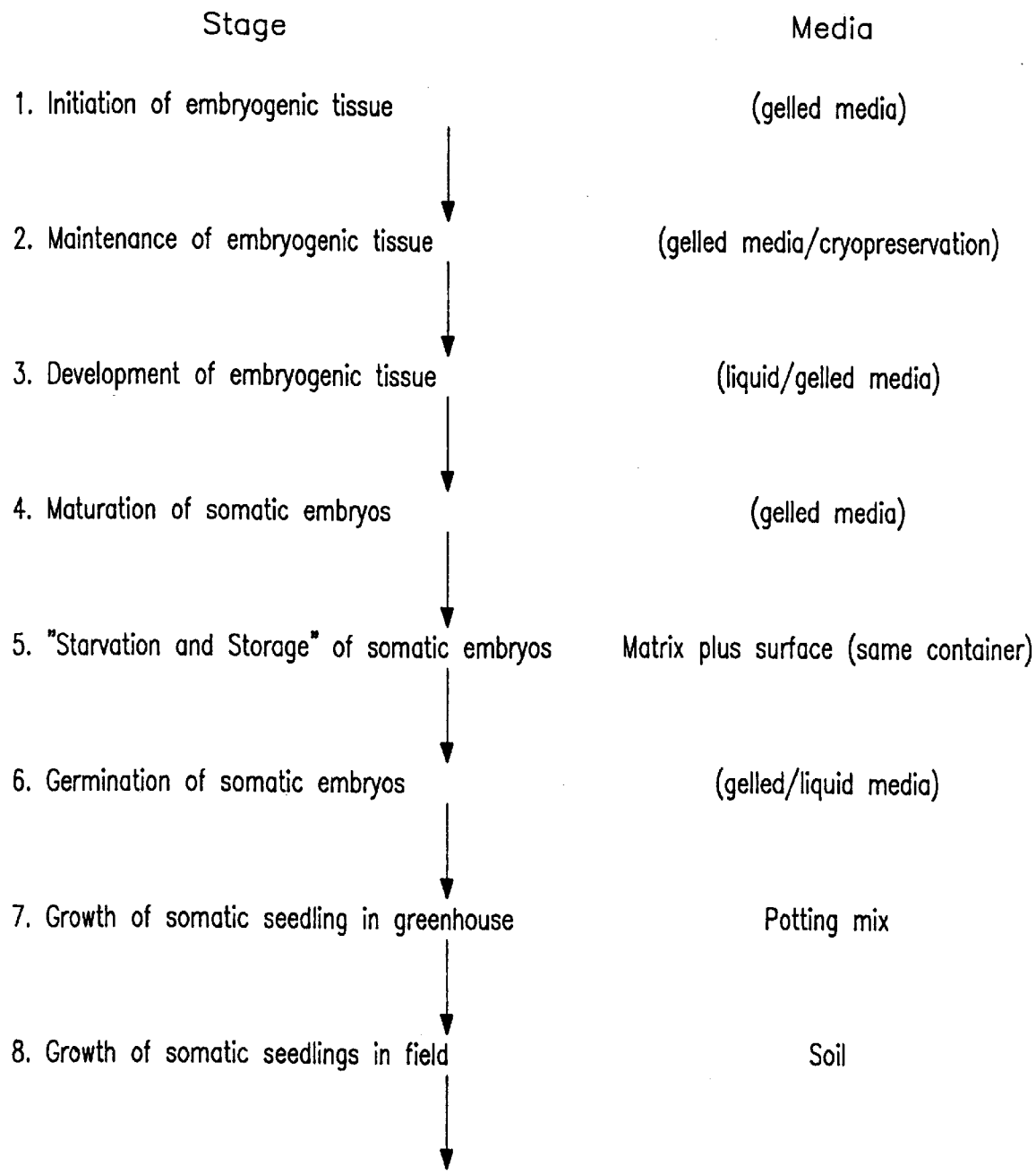

STARVATION AND STORAGE OF MATURE SOMATIC EMBRYOS

TECHNICAL FIELD

The present invention relates to methods and apparatus useful in the production of mature conifer somatic embryos capable of being germinated as required.

BACKGROUND ART

New Zealand Patent Specification No. 237009 (PCT/CA90/00241 published as WO 91/01629) of British Columbia Research Corporation discloses the background to the clonal propagation of trees and other plants and discusses difficulties arising from precocious germination of embryos in vitro which does have an adverse effect on seed germination when germination is desired.

British Columbia Research Corporation in the aforementioned New Zealand Patent Specification No. 237009 (U.S. Pat. No. 5,183,757) discloses a process for a propagation of conifer somatic embryos which includes the steps of differentiating somatic embryos in contact with a growth medium, separating the somatic embryos from said medium, and germinating the somatic embryos, the process being characterised from prior art processes in that the embryos are matured on said medium and are partially dried prior to germination by exposing mature embryos separated from the said medium to an atmosphere having greater than 80% humidity. The species used for an example is spruce. The Specification discloses the establishment of such a humidity by providing in a closed area the presence of water either in the form of water itself or as part of an aqueous solution of a salt. The pregermination treatments included placing mature embryos in petri dishes on water-saturated kimpaks on petri dishes at room humidity or in 6 wells of a 12 well petri dish with the other 6 wells filled three quarters full with sterile water.

We have found that when this method is applied to pine, all embryos elongated and some became partially green even though stored in the dark at all times (unpublished). This rendered them unsuitable for germination as they had already partially germinated precociously.

U.S. Pat. No. 5,238,835 granted Aug. 24, 1993 (University of Guelph) provides additional background as to the use of embryogenesis in the creation of artificial "seeds". There is reference therein to U.S. Pat. No. 4,615,141 (Janick and Kitto) concerning methods for enhancing desiccation tolerance in somatic embryos.

U.S. Pat. No. 5,238,835 itself discloses in relation to Alfalfa and Brassica a pregermination treatment comprising the application of an environmental stress to cause the embryos to synthesise abscisic acid in sufficient quantity to cause expression of desiccation tolerance in the embryos. The application of environmental stress is stated as comprising one or more of (i) slow gradual desiccation (ii) low temperature (iii) nutrient starvation (iv) heat stress, and (v) osmotic stress.

The benefits stated are a) prolonged storage in a dormant state and b) enhanced vigour of the resultant seedling. It is stated that when dry the metabolism of the embryo is arrested and thus the utilisation of valuable storage reserves and the precocious growth of the seedling is prevented. It is stated as anticipated that tissue prepared and dried as described in the procedure could be stored in a similar way and for similar periods of time compared to "true" seeds. It is additionally stated that there is enhanced vigour of the seedling from a dry embryo compared to that produced by an embryo which follows a developmental path analogous to precocious germination.

U.S. Pat. No. 5,238,835 indicates that once tolerance has been induced the embryo can be air dried to moisture contents less than 20% water or equivalent to those observed in true seeds. Such dried embryos are stated as being capable of being stored in cool dry conditions such as those used for storing true seed.

There is an indication that the procedure necessarily is of two parts.

(i) the subjection of the embryos to abscisic acid, and (ii) thereafter, (eg. after about 5 to 14 days of the exposure to abscisic acid) the adoption of a "fast" or "slow" drying procedure.

The abscisic acid treatment (i) in the preferred form is as a result of the aforementioned subjection to environmental stress causing the embryos to synthesize the abscisic acid required by the step (i).

It is stated that "fast drying" of step (ii) is achieved either by air drying or by drying in a low humidity (45% relative humidity) chamber. It is also stated that "slow drying" of step (ii) is achieved by placing embryos in a series of desiccators each with a controlled humidity for a total of 6 days. For the 1st day of drying embryos are kept at 97% humidity and are transferred daily to chambers with 87%, 75.5%, 62.5%, 50.5% and finally to 43% relative humidity. This invention does not require any "drying" of embryos.

Earlier U.S. Pat. Nos. 5,041,382, 4,957,866, 5,036,007, 5,236,841 and PCT WO 93/1166 refer to the pretreatment of embryos with osmotic agents (such as Polyethyleneglycol PEG). These are claimed to enchance the quality of somatic embryos at different stages including the mature stage and to allow efficient desiccation of embryos and subsequent germination. We have found these and other osmotic treatments unnecessary for the purpose of this invention and the somatic embryogenesis process in general, and use of them inhibits the development of embryos, including the maturation stage (data not shown). The tissue grows into an undesirable form (fluffy-like), and formation of embryos at any stage is inhibited in experiments to date.

Other authors also do not use a desiccation protocol (Zelu, M. A., Bastien, C., Klimaszewska, K. and Chacest, P (1994) An improved method for somatic plantlet production in hybrid larch: Part 2, Control of germination and plantlet development. Plant Cell, Tissue and Organ Culture 36(1): 117–127).

PCT WO 93/1166 also claims the preferred moisture content of conifer somatic embryos as ranging between 10–55% accomplished with the use of osmotic agents (eg; PEG) in the medium, in order to store somatic embryos for long periods of time. The present invention provides an alternative to the methods of PCT W093/1166, ie; we require the addition of osmotic agents and we avoid the requirement for lower moisture content in the 10–55% range.

New Zealand Forest Research Institute (FRI) patents [South African Patent No. 93/4807] states that a pre-germination media prepared with a gelling agent or no pre-germination between maturation of embryos on ABA-containing media (4—see FIG. 4) and germination of embryos (6—see FIG. 4) are the preferred methods. When these methods were tested 81.3% of embryos stayed white or became partially green after 4 weeks of germination, and only 18.7% germinated. In this respect please see Table 1.

TABLE 1

Germination of radiata pine embryos using protocols in FRI patents

| Clone No. | Total Embryos | Low Quality Embryos | High Quality Embryos | Percentage Germination after 4 weeks |
|---|---|---|---|---|
| A93 | 55 | 7 | 33 | 27.3 |
| A93-17 | 24 | 2 | 15 | 29.2 |
| C93-4 | 43 | 2 | 19 | 51.2 |
| D93-199 | 236 | 27 | 174 | 14.8 |
| E93-2 | 78 | 18 | 45 | 19.2 |
| I93-22 | 217 | 55 | 134 | 12.9 |
| Total | 653 | 222 | 420 | 18.7 |

Other prior art refers to storage of embryogenic tissue at the earlier maintenance stage of embryogenesis @ 5, 10, 15, 25° C. (2—see FIG. 4) by Y. S. Park, S. W. Pond & J. M. Bonga (1994): Somatic embryogenesis in white spruce (Picea glauca): genetic control of somatic embryos exposed to storage, maturation treatments, germination and cryopreservation. Theor. Appl. Genet. 89:742–750.

DISCLOSURE OF INVENTION

The present invention has given rise to apparatus and methods which provides a requirement for fewer steps than those disclosed in U.S. Pat. No. 5,238,835 and moreover immediately allows embryos as they are removed from their nutrient source to be isolated from contamination and stored for prolonged periods without drying and without further intervention yet still have the survivability and viability rates as disclosed in U.S. Pat. No. 5,238,835.

The present invention therefore is directed to methods and apparatus useful in such a pregermination treatment for somatic embryos which will at least provide the public with a useful choice.

While the procedures of the present invention originally had gone to storage procedures for synchronisation we have now surprisingly found that the act of cool storage in accordance with the present invention is of significance in achieving greater germination rates over non-stored embryos and likely over embryos stored by other storage procedures (Table 2).

TABLE 2

| Clone number | Plants in pottle | Plants in soil | 0 days storage Germination % age | 1–138 days storage Germination with storage, % age for storage |
|---|---|---|---|---|
| K94-165 | 361 | 74 | 20.5 | 70.7 |
| K94-166 | 216 | 52 | 24.1 | 58.6 |
| E94-108 | 967 | 211 | 21.8 | 39.4 |
| TOTAL | 1544 | 337 | 21.8 | 60.9 | ie. Consistently low for 0 days storage.

Also, by way of example, 60,000 mature somatic embryos from 38 clones were starved and stored by the present invention and overall germination of 86.6% was achieved. Clonal differences as shown in Table 2 were significant.

The present invention also is therefore directed to means and methods likely to provide enhanced germination rates for conifers.

In a first aspect the present invention consists in a storage treatment of (ie; a method of treating) mature conifer somatic embryos to provide embryos that are viable after a period of storage, should they be so stored, which treatment (method) comprises supporting the embryos out of direct contact with any nutrient containing medium and any liquid(s) on a surface that is substantially porous to water vapour, substantially immediately (eg; within a period of less than, say, 30 minutes or immediately) at least substantially sealing a gas environment about said embryos and said surface by means spaced from said embryos and said surface, said substantially sealed environment also including therein water and/or a water containing matrix spaced from the embryos, then (i) holding for at least substantially all of said period of storage the substantially sealed embryo containing environment at a temperature or temperatures in the range of from 15° C. to less than 30° C. [eg; in a standard tissue culture cabinet or controlled environment room]; or (ii) holding for at least substantially all of said period of storage the substantially sealed embryo containing environment at a temperature or temperatures in the range of from about 2° C. to 15° C., and preferably 5° C. to 10° C. [eg; in a refrigerator, cool room or chiller]; or (iii) holding for a period of storage the substantially sealed embryo containing environment for a multiple of periods of storage, at least one being as in (i) and at least one as in (ii).

Preferably there is storage at least in part at the conditions of (ii).

Preferably there is no free water sealed in the gas environment, ie. preferably is absorbed by the matrix.

Preferably storage in form (i) is for less than 6 weeks.

Preferably storage in form (ii) is from 1 day to about 5 years eg. about 6 months.

Preferably storage form (iii) is for a period of less than 5½ years.

Preferably said conifer embryos are those of *Pinus radiata* (or Monterey pine) hybrids of *Pinus radiata* and genetically modified *Pinus radiata*. This procedure is also applicable to other conifer species, viz, loblolly pine, Douglas fir, spruce species, etc and, of course, hybrids or genetically modified versions thereof.

Preferably said surface porous to water vapour, in one form, is a porous membrane.

Preferably said surface is defined by a PHYTACELL membrane.

Preferably the membrane is preferably a microporous polypropylene membrane, eg; a PHYTACELL membrane raft round marketed as SIGMAWARE™ (catalogue number M4380) available from Sigma Chemical Co, St Louis, Mo. 63178, USA.

In another form a simple surface defining membrane can be used. An example is a sheet of open cell foam plastics, rubber, cellulosic, wool, rockwool, sorbarod or similar material or a sheet of an appropriate woven fabric of any thickness depending on size of sterile tissue culture container, for example, 5mm thick, 0.5 to 2.0 mm (preferably with a pore size 0.5–1.0 mm). An example of a suitable plastics is polypropylene or other sterilisable plastic. Ideally the material is sterilizable.

Preferably said means defining a surface is supported on (directly or indirectly) the inside surface of a petri dish or plate [hereafter "dish"] or other sterile enclosure.

Preferably said substantially sealed gas environment is created by providing a lid or cover to said petri dish and if required additionally sealing about the petri plate and the lid or cover, [eg. by the use of a cling film of a plastics material such as, for example, GLADWRAP™ or an adhesive tape].

In some forms multiple surfaces are defined in a single sterile enclosure. For example a plurality of trays or dishes (eg; petri dishes) could be arrayed (with or without stacking) in a large sealable container, ie; the individual dishes are not themselves individually sealed or there could be multiple surfaces within a petri dish or other container.

The preferred height of any such containers (eg; dishes whether sealable individually or not) is from 10 to 20 mm in order to allow stacking for space efficiency during storage.

Preferably the gas environment is of air.

Preferably the sealed environment is of air having a relative humidity for the temperature at which the environment is kept of greater than 80% R.H. (preferably above 90% R.H.).

Preferably said water containing matrix is a matrix of cellulosic fibres.

Preferably said water containing matrix is paper.

Preferably said water containing matrix is a sheet of paper positioned beneath the means defining said surface and preferably on the base surface of a petri dish or other sterile enclosure.

Preferably said water containing matrix is a round disc of a filter paper.

Preferably said water containing matrix is a matrix impregnated with sterilised distilled water. In other forms of the present invention however, the water can be part of an aqueous solution, eg. of a salt.

Preferably the embryos are placed on said surface at ambient temperatures of from about 20° C. to 28° C. and preferably about 25° C. and said substantially "immediate at least substantial sealing of the gas environment" occurs within a period of less than 30 minutes (preferably immediately) after such placement and immediately upon such at least substantial sealing of the gas environment or indeed even as the environment is being substantially sealed the ambient temperature is in the range of from 20° C. to 28° C. (preferably about 25° C.). Typically, this is a standard tissue culture cabinet or room with environmental sensors and control.

Preferably they are stored at 2° C. to 15° C.

They may be stored at temperatures above 15° C. but below 30° C. (preferably below 28° C.) for up to about 6 weeks, preferably 2 to 4 weeks after which they may be used or stored at from 2° C. to 15° C., preferably 5° C. to 10° C. Typically this is in a refrigerator, cool room or chiller.

Preferably the procedure is that immediately subsequent to the at least substantial sealing of the gas environment the assembly is placed in a refrigerated environment.

Preferably the embryos on said surface(s) are no greater than one embryo deep.

Preferably said embryos on said surface are out of contact with one another.

Preferably the storage treatment is conducted as far as it is conveniently appropriate in sterile surroundings.

In a further aspect the present invention consists in, as part of a germination process of conifers from somatic embryos, the use of a storage treatment as previously stated and the subsequent germination of the (cool) stored embryos.

In yet a further aspect the present invention consists in wood or other products derived from trees germinated by a process as previously stated or the trees themselves.

In yet a further aspect the present invention consists in apparatus suitable for use in a treatment as aforesaid or a procedure hereafter described comprising in combination and/or in assembly a closeable petri dish or other sterile enclosure, a matrix impregnated with water or capable of absorbing water and means to define a surface that is substantially porous to water vapour capable together with said matrix of being enclosed in said petri dish or other sterile enclosure yet the surface providing sufficient space for embryos away from any surface of said closeable petri dish or other sterile enclosure and also out of contact with the matrix impregnated with water.

Preferably the assembly includes water (preferably not free water, ie; it is in the matrix or is vapour) or a diluted nutrient salt solution.

Preferably the assembly includes water where, for a petri dish there is 3 mls sterile water per 90 mm wide×20 m (ht) dish (volume 127 cc). Preferably therefore there is about 0.02 ml water per cc volume of the container.

Preferably the apparatus is an assembly which also includes embryos on said surface.

Preferably said matrix is a disc or several discs (eg; 3 discs and 3 mls of water) of a filter paper. Preferably Whatman #1.

Preferably said means defining a surface is capable of being enclosed in said closeable petri dish or sterile enclosure above said matrix.

Preferably said combination or assembly also includes tape or clingfilm for sealing or substantially sealing the closed petri dish or sterile enclosure after embryos have been placed on the surface therein or a cling film wrap.

In a particularly preferred form the combination or assembly is of a closeable petri dish or sterile enclosure, a paper (eg. filter paper) disc or other sheet (or indeed other cellulosic or other fibrous material sheet) placed on a surface inside the petri dish or sterile enclosure and having placed thereon a sheet, block or other form of water vapour permeable matrix (eg. a sheet of an open cell foamed plastics material or woven plastics material) and the mature somatic embryos supported on that surface, the matrix having the effect of keeping the embryos away from any contact with the inside surface of the petri dish or sterile enclosure and out of contact with any water.

Preferably said combination or assembly is in a storage environment and preferably a cold storage environment.

In a further aspect the present invention consists in a starvation and storage regime or procedure for use in the preparation of viable somatic embryos capable of being germinated, said procedure involving placing the embryos out of contact with any nutrient containing medium and any liquid(s) on a surface that is substantially porous to water vapour defined by appropriate means positionable in a petri dish or other sterile container over and/or above a paper or other matrix impregnated with water, covering and sealing the petri dish or other sterile container without contacting the embryos and refrigerating the least substantially sealed assembly for a storage period prior to removal for germination, such storage being at a temperature within the range of from 2° C. to 15° C., preferably 5° C. to 10° C.

In another aspect the present invention consists in a method of enhancing the germination prospects of mature conifer somatic embryos which method comprises prior to attempting germination (eg; by providing a germination inducing and supporting environment), (I)(a) supporting the embryos out of direct contact with any nutrient containing medium and any liquid(s) on a surface that is substantially porous to water vapour, (b) substantially immediately at least substantially sealing a gas environment about said embryos and said surface by means spaced from said embryos and said surface, said substantially sealed environment also including there within water and/or a water containing matrix spaced from the embryos, and (II) thereafter storing the substantially sealed embryo containing environment at a temperature or temperatures in the range of from about 2° C. to 15° C., and preferably 5° C. to 10° C.

Preferably said storage is from 1 day to 5 years.

Preferably said storage follows an initial holding at a temperature or temperatures of from 15° C. to 30° C.

Preferably step (I) is as previously defined.

In still a further aspect the present invention consists in a method of germinating a conifer comprising adopting a method of enhancing the germination prospects of mature somatic embryos as previously defined and thereafter (III) providing for the embryo the conditions for germination and allowing germination.

Preferably steps (II) and (III) are performed without movement of the embryos from the substrate surface.

Preferably step (III) involves presenting into the previously sealed environment a germination inducing and sustaining liquid medium.

BRIEF DESCRIPTION OF DRAWINGS

Preferred forms of the present invention will now be described with reference to the accompanying drawings in which;

FIG. 4 shows a flow diagram of the preferred eight steps.

The present invention includes the "starvation and storage" step (v) identified in the following process sequence and as shown in FIG. 4. Stage

| Media | Stage |
|---|---|
| 1. Initiation of embryogenic tissue | (gelled media) |
| 2. Maintenance of embryogenic tissue | (gelled media/cryopreservation) |
| 3. (Optional) Development of embryogenic tissue | (liquid/gelled media) |
| 4. Maturation of somatic embryos | (gelled media) |
| 5. "Starvation and Storage" of somatic embryos | Matrix plus surface (same container) |
| 6. Germination of somatic embryos | (gelled/liquid media) |
| 7. Growth of somatic seedling in greenhouse | Potting mix |
| 8. Growth of somatic seedlings in field | Soil |

Stages 1–5 are carried out in the laboratory under sterile conditions. Stage 6 is either sterile or non-sterile in the laboratory or greenhouse and Stages 7 and 8 are carried out in the greenhouse and nursery.

The present invention also relates to a combination of Stages 5 and 6 to enhance germination rate and to any selection of groupings of Stages 1 to 8 provided any such grouping includes Stages 5 or Stages 5 and 6. Embryos produced via the invention outlined in New Zealand Patent Application No. 272211 can also be used in this invention (Stage 5) and any selection of Stages 6–8.

Both the starvation and storage treatment are carried out in the same sterile container (FIG. 4) and are thus can be considered one step. It is only the environment around the container which changes.

Figure 1:
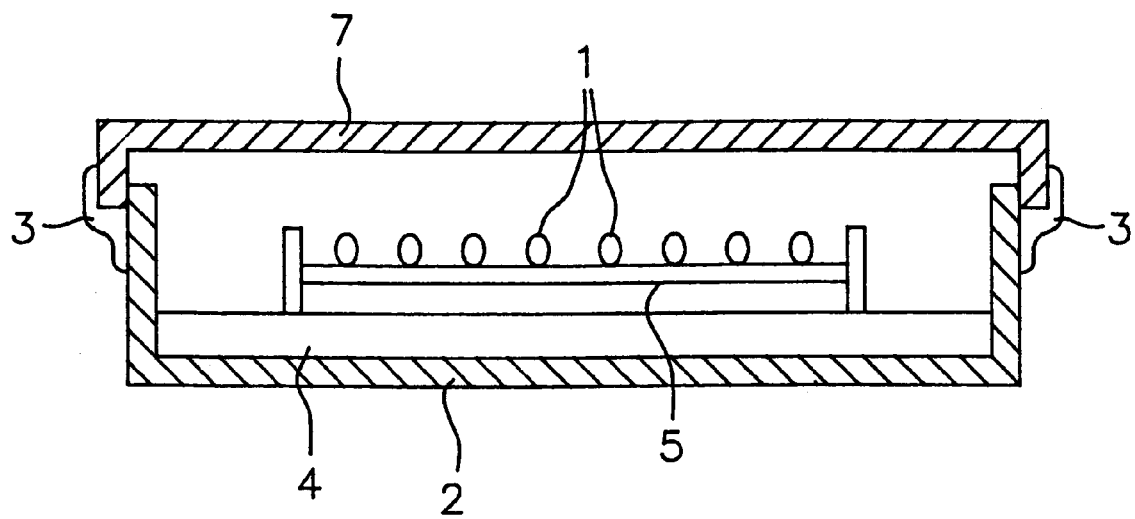
FIG. 1 is an elevational cross section of a first preferred form of assembly in accordance with the present invention showing a sealed petri dish having placed on the bottom surface thereof a wet filter paper disc and positioned thereon a PHYTACELL membrane which carries the somatic embryos out of contact with the filter paper and away from the inside surface of the petri dish, the filter paper having being impregnated with sterile water prior to or subsequent to its placement in the petri dish.

In FIG. 1 the petri dish lid 1 (but it could be part of any other closeable environment defining enclosure) and the petri dish base 2 are sealed preferably using an adhesive tape 3. Alternatively a cling wrap material could be wrapped about the enclosure.

Figure 2:
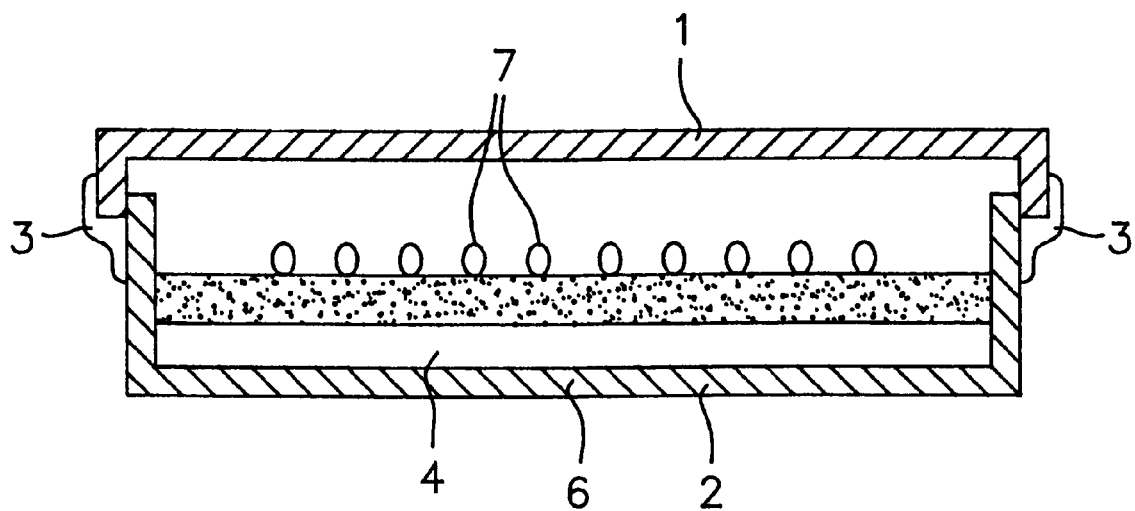
FIG. 2 is a similar arrangement to that FIG. 1 but this time showing the PHYTACELL membrane having being replaced by a sheet of an open cell plastics foam material (eg. polypropylene)
Figure 3:
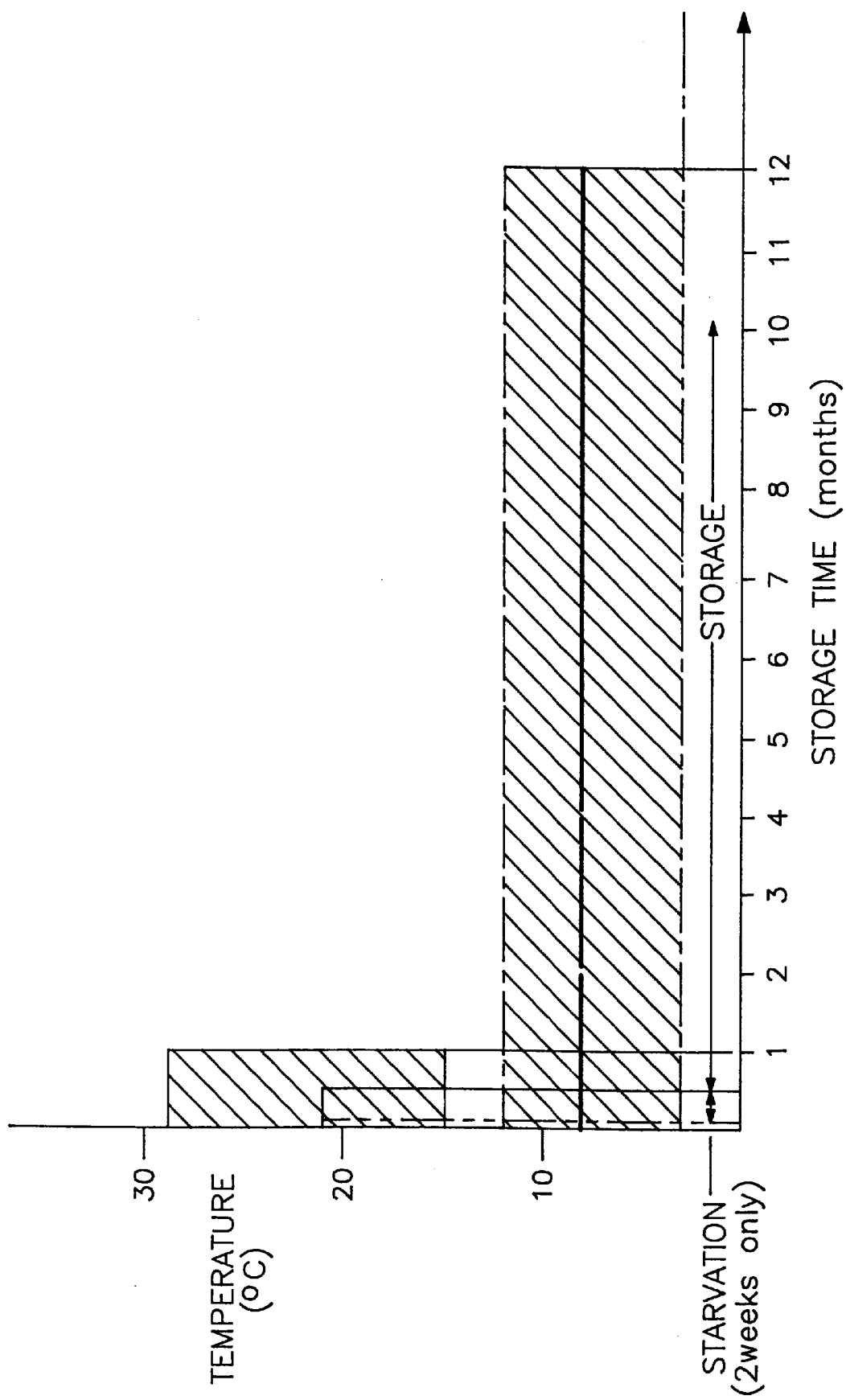
FIG. 3 is a graph showing temperature (° C.) against storage time (months) using the procedure of the present invention.

A disc or other shape of water containing matrix 4 is preferably placed on the bottom surface of the petri dish 2 and supports thereabove either a PHYTACELL filter (porous matrix) 5 as shown in FIG. 1 or a sheet of open cell foamed plastics material (porous matrix) 6 as shown in FIG. 2 which in turn support the somatic embryos 7.

Table 3 shows embryo density achievable with different dish sizes.

TABLE 3

| | Small petri dish | Large petri dish |
|---|---|---|
| Diameter | 5.8 cm | 9.0 cm |
| Area of matrix of surface | 26.4 cm$^2$ | 63.5 cm$^2$ |
| Volume of dish | 39.6 cm$^3$ | 127 cm$^3$ |
| Number of embryos/dish | 30–40 | 80–100 |
| Number of embryos cm$^2$ | (1.13–1.57) preferably 1.35 | (1.3) (1.26–1.57) preferably 1.4 |

Other arrangements within any sealed enclosure are possible including placement of the water containing matrix along side the means which defines the water vapour permeable surface on which the somatic embryo rest.

The advantage of having a water impregnated matrix is to provide a source of water vapour for the embryos on the surface spaced out of contact with water without real concern of direct contact with free water allowing approximately 10% lower moisture content (Table 6).

The preferment however is to provide means which defines the surface on which the somatic embryos sit which has little tendency to absorb water enclosed in the sealed environment and in this respect the presence of the matrix which has already absorbed the material is of assistance although some free water (eg. as ice, condensation, etc.) could have accumulated inside.

The somatic embryos to be used in the storage preparation process of the present invention, then stored and subsequently to be germinated are derived from different nutrient media used in States 1–4, FIG. 4.

Because our aim is commercial production, somatic embryos usually have to be stored for a certain period so flat germination and subsequent growing on is synchronised with natural annual planting and growing seasons.

Three different clones of radiata were tested under different photoperiods and ranges of storage periods (0 to 138 days) to comprehend the effect of cold storage (particular at condition (ii) aforesaid) on survival rates and growth rate of somatic seedlings. Two weeks of pre-germination treatment (starvation) in room temperature was given prior to cold storage. The seedlings had been germinated and were transplanted to the greenhouse for acclimitisation and growing on.

Totals of 9,504 somatic seedlings were planted out in seedling trays. Table 4 sets out the 3 radiata clones and their tray densities.

TABLE 4

Number of Trays and Somatic Seedlings by Treatment/Clone No.
(Experimental design for Table 5)

| Clone No./Treatment | 1 | 2 | 3 | 4 | Total |
|---|---|---|---|---|---|
| E94-108 | 6 trays | 6 trays | 6 trays | 6 trays | 24 trays |
|  | 792 seedlings | 792 seedlings | 792 seedlings | 792 seedlings | 3168 seedlings |
| K94-165 | 6 trays | 6 trays | 6 trays | 6 trays | 24 trays |
|  | 792 seedlings | 792 seedlings | 792 seedlings | 792 seedlings | 3168 seedlings |
| K94-166 | 6 trays | 6 trays | 6 trays | 6 trays | 24 trays |
|  | 792 seedlings | 792 seedlings | 792 seedlings | 792 seedlings | 3168 seedlings |
| Total | 18 trays | 18 trays | 18 trays | 18 trays | 72 trays |
|  | 2376 seedlings | 2376 seedlings | 2376 seedlings | 2376 seedlings | 9504 seedlings |

Each somatic seedling was given individual growth rates/scores of 1 to 5 as follows after 6 weeks of planting to seed trays.

| | |
|---|---|
| Growth rate 1 | No growth at all. |
| Growth rate 2 | Little growth with good root development. |
| Growth rate 3 | Good growth with less than 10 hypocotyls. |
| Growth rate 4 | Big seedlings with more than 10 hypocotyls. |
| Growth rate 5 | Very big seedlings with hypocotyls elongated. |

The result is shown in Table 5.

Mature somatic embryos of white spruce (Picea glauca) from 2 clones or cell lines were subjected to the starvation treatment for 14 days and the storage treatment for 14 days and 100% germination occurred in the germination medium. The germination medium was the same as the used for radiata pine.

The length of the storage periods did not affect the survival and growth rates of somatic seedlings. Differences are shown between the clones and treatments. See Table 4. Clonal effects were greater than any other effect.

Mature somatic embryos were able to be stored up to 365 days at 7° C. after 2 weeks of starvation, and 100% germi-

TABLE 5

Survival after germination and growth rate score for 3 clones used during different periods of time in storage - extract from following

| | E94-108 | | K94-165 | | K94-166 | |
|---|---|---|---|---|---|---|
| Days in Storage | % survival after germination (total embryos) | Growth Rate Score | % survival after germination (total embryos) | Growth Rate Score | % survival after germination | Growth Rate Score |
| 0 | 82.9 (286) | 2.1 | 84.5 (110) | 3.2 | 100.0 (52) | 3.1 |
| 4 | 83.9 (255) | 2.1 | 93.5 (231) | 2.7 | 93.8 (48) | 2.4 |
| 5 | — | — | 87.2 (47) | 3.0 | 95.0 (80) | 2.3 |
| 7 | 93.8 (32) | 2.7 | 94.0 (1507) | 2.9 | — | — |
| 8 | 70.5 (533) | 2.3 | 81.8 (99) | 2.5 | 100.0 (76) | 3.6 |
| 11 | — | — | — | — | 96.2 (79) | 2.7 |
| 18 | 81.2 (48) | 1.8 | 93.5 (108) | 3.0 | 97.6 (42) | 3.5 |
| 19 | 82.8 (169) | 1.4 | 95.4 (174) | 3.1 | — | — |
| 20 | 54.7 (415) | 2.3 | 95.1 (128) | 2.5 | 80.0 (5) | 3.3 |
| 22 | — | — | 84.2 (19) | 1.8 | — | — |
| 25 | 50.3 (513) | 2.1 | 100.0 (25) | 3.5 | 87.6 (1897_ | 2.7 |
| 28 | 64.8 (54) | 2.0 | 90.7 (311) | 2.6 | 89.8 (86) | 2.8 |
| 48 | 94.3 (140) | 2.1 | — | — | — | — |
| 82 | 100.0 (9) | 3.0 | — | — | 97.4 (155) | 2.9 |
| 91 | 45.5 (420) | 2.4 | 93.8 (16) | 3.0 | — | — |
| 92 | — | — | — | — | 53.0 (40) | 2.6 |
| 93 | — | — | — | — | 86.3 (51) | 2.9 |
| 96 | 85.7 (14) | 2.0 | — | — | — | — |
| 97 | 73.5 (49) | 2.7 | — | — | — | — |
| 98 | 86.5 (52) | 2.9 | 98.1 (103) | 2.9 | — | — |
| 110 | — | — | — | — | 85.4 (103) | 3.0 |
| 111 | 83.3 (6) | 1.2 | — | — | — | — |
| 112 | 60.2 (83) | 2.5 | — | — | 94.4 (195) | 3.2 |
| 113 | 87.3 (55) | 3.1 | — | — | — | — |
| 115 | — | — | — | — | 91.9 (74) | 3.2 |
| 116 | 69.0 (42) | 2.5 | — | — | — | — |
| 128 | — | — | — | — | 93.9 (213) | 3.0 |
| 132 | 66.7 (60) | 2.4 | — | — | 97.2 (36) | 3.3 |
| 133 | 85.0 (20) | 2.9 | — | — | — | — |
| 134 | — | — | — | — | 88.9 (18) | 4.2 |
| 135 | 61.0 (41) | 1.8 | — | — | 91.7 (12) | 3.5 |
| 138 | 65.4 (26) | 2.5 | — | — | — | — | nation was obtained without any defects. Moisture contents of mature somatic embryos The moisture contents of the following groups of 50 randomly selected mature embryos were measured.
1. Embryos placed on moist filter paper for 30 days.
2. Embryos placed on foam with moist filter paper underneath for 30 days.
3. Zygotic embryos imbibed for 24 hours.

There was significant difference in moisture contents between somatic embryos and zygotic embryos. (See Table 6).

Table 6 compares water content between zygotic and somatic embryos (the latter being obtained by the process described).

There is approximately a 10% difference in Treatments 2 and 3. This is thought to be important for effective subsequent cool storage and avoiding precocious germination.

TABLE 6

Comparison of the percentage moisture content of zygotic and somatic radiata pine embryos

|  | Moisture Content (%) |
|---|---|
| Zygotic embryos | 38.9 |
| Somatic embryos-fip (U.S. Pat. No. 5183757) | 87.8 |
| Somatic embryos-fip and foam | 78.3 |

When somatic embryos were desiccated to moisture contents less than 50%, they did not germinate on germination media (data not shown). This is in agreements with *Pinus radiata* somatic embryos not requiring a desiccation method in order to germinate and hence our use of the term "starvation" and not "desiccation". Pre-germination treatment for embryos was a starvation treatment rather than desiccation, and our simple treatment offered embryos an ideal environment with minimal extra equipment and handling, thus reducing handling costs. Both the starvation and storage treatments are carried out in the same sterile container (FIG. 4) and are thus considered one step. It is only the environment around the container which changes. Embryos were retained in this treatment for 1–6 weeks. Whilst embryos on filter paper only had a moisture content of 87.8% (Table 2), they partially germinated and were not desirable whereas those elevated with foam had a moisture content of 78.3% and these remained white, more similar to a zygotic embryo.

New Zealand Patent Specification 232834 of Weyerhaeuser Company discloses one appropriate method for providing somatic embryos useful in the present invention.

The most preferred source is that disclosed in Forest Research Institute (of New Zealand) Australian Patent Application No. 37150/93 filed Apr. 23, 1993. The full content of the aforementioned New Zealand and Australian Patent Specifications are hereby here included by way of reference.

It is envisaged by adoption of the procedures of the present invention viable mature somatic embryo of all conifer species can be stored for prolonged periods thus enabling the preparation of sufficient mature somatic embryo so that economic planting stock quantities are available at the right time of the year for field planting.

What is claimed is:

1. A method of treating mature conifer somatic embryos to provide embryos that are viable after a period of storage, which method comprises:
   supporting the embryos out of direct contact with any nutrient containing medium and any liquid on a surface that is substantially porous to water vapour;
   substantially immediately substantially sealing a gas environment about said embryos and said porous surface by means spaced from said embryos and said porous surface, said substantially sealed environment including therein water spaced from the embryos, then
   (i) starving the embryos while in said substantially sealed embryo containing environment at a temperature in the range of 15° C. to 30° C.
   (ii) storing the embryos after the starvation step while still in said substantially sealed embryo containing environment at a temperature in the range of 2° C. to 15° C.

2. The method of claim 1 wherein said water is in the form of a water containing matrix.

3. The method of claim 1 wherein starving in step (i) is for less than 6 weeks.

4. The method of claim 1 wherein storage in step (ii) is from 1 day up to 5½ years.

5. The method of claim 1 wherein said conifer embryos are those selected from the group consisting of *Pinus radiata* (Monterey pine), loblolly pine, Douglas fir and spruce species, or hybrids or genetically modified versions thereof.

6. The method of claim 1 wherein said surface porous to water vapour is a porous membrane.

7. The method of claim 1 wherein said surface porous to water vapour is selecting from a group consisting of a sheet of a porous plastic rubber or cellulosic material, wool, rockwool, sorbarod, or a sheet of a woven fabric.

8. The method of claim 6 wherein said means defining a surface is supported on an inside surface of a petri dish.

9. The method of claim 8 wherein said substantially sealed gas environment is created by providing a lid on said petri dish.

10. The method of claim 6 wherein there are multiple surfaces porous to water vapour.

11. The method of claim 10 wherein said multiple surfaces consist of a plurality of trays are arrayed in a large sealable container without the individual trays being individually sealed.

12. The method of claim 1 wherein the gas environment is of air.

13. The method of claim 1 wherein the sealed environment is of air having a relative humidity for the temperature at which the environment is kept of greater than 80% R.H.

14. The method of claim 2 wherein said water containing matrix is a matrix of cellulosic fibres.

15. The method of claim 14 wherein said water containing matrix is paper.

16. The method of claim 15 wherein said water containing matrix is a sheet of paper positioned beneath said porous surface.

17. The method of claim 2 wherein said water containing matrix is a matrix impregnated with a sterile aqueous solution.

18. The method of claim 1 further comprising the steps of placing the embryos on said porous surface at ambient temperature of from 20° C. to 28° C. and said substantially immediate sealing occurs within a period of less than 30 minutes after such placement and immediately upon said substantial sealing of the gas environment.

19. The method of claim 18 wherein a standard tissue culture cabinet with environmental sensors and control is used.

20. The method of claim 19 wherein said culture cabinet is maintained at 2° C. to 15° C.

21. The method of claim 1 wherein the embryos are stored at temperatures above 15° C. but below 30° C. for up to about 6 weeks after which they may be stored at from 2° C. to 15° C. in a refrigerator.

22. The method of claim 1 where immediately subsequent to the substantial sealing of the gas environment the assembly is placed in a refrigerated environment.

23. The method of claim 1 wherein the embryos on said surface are no greater than one embryo deep.

24. The method of claim 23 wherein said embryos on said surface are out of contact with one another.

25. The method of claim 1 wherein the storage treatment is conducted as far as it is conveniently appropriate in sterile surroundings.

26. Apparatus suitable for use in the method of claim 1 comprising, in combination:
    a closeable petri dish;
    a matrix impregnated with water;
    means to define a surface that is substantially porous to water vapour capable together with said matrix of being enclosed in said petri dish yet the surface providing sufficient space for embryos away from any surface of said closeable petri dish and also out of contact with the matrix impregnated with water.

27. The apparatus of claim 26, which also includes embryos on said porous surface and water at least partly in said matrix.

28. Apparatus of claim 26, wherein said matrix is a disc or several discs of a filter paper.

29. Apparatus of claim 26, wherein the combination is of a closeable petri dish, a fibrous sheet placed on a surface inside the petri dish and having thereon a water vapour permeable matrix and having the mature somatic embryos supported on that surface, the matrix having the effect of keeping the embryos away from any contact with the inside surface of the petri dish and out of direct contact with any liquid water.

\* \* \* \* \*